US00PP31909P2

(12) United States Plant Patent
Greyvenstein

(10) Patent No.: US PP31,909 P2
(45) Date of Patent: Jun. 23, 2020

(54) ***CUPHEA* PLANT NAMED 'BALHOELREL'**

(50) Latin Name: ***Cuphea* hybrid**
Varietal Denomination: Balhoelrel

(71) Applicant: Ball Horticultural Company, West Chicago, IL (US)

(72) Inventor: Ockert F. C. Greyvenstein, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/501,924

(22) Filed: Jul. 3, 2019

(51) Int. Cl.
*A01H 5/02* (2018.01)
*A01H 6/00* (2018.01)

(52) U.S. Cl.
USPC ..... Plt./420

(58) Field of Classification Search
USPC ..... Plt./263.1, 420
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Cuphea* plant named 'Balhoelrel', characterized by its medium red and yellow-green colored tubular flowers having small dark purple-colored petals, dark green-colored foliage, and moderately vigorous, spreading growth habit, is disclosed.

1 Drawing Sheet

Latin name of genus and species of plant claimed: *Cuphea* hybrid.

Variety denomination: 'Balhoelrel'.

BACKGROUND OF THE INVENTION

The present invention relates to a new and distinct cultivar of *Cuphea* plant botanically known as *Cuphea* hybrid and hereinafter referred to by the cultivar name 'Balhoelrel'.

The new cultivar originated in a controlled breeding program in Guadalupe, Calif. during June 2014. The objective of the breeding program was the development of *Cuphea* cultivars with shortened rooting time especially under cooler temperatures, and a moderately vigorous, spreading growth habit.

The new *Cuphea* cultivar is the result of cross-pollination. The female (seed) parent of the proprietary *Cuphea* breeding selection coded w14-0006, not patented, characterized by its bright scarlet-colored tubular flowers having a white-coloration at the tube opening, medium green-colored foliage, and moderately vigorous, upright growth habit. The male (pollen) parent of the new cultivar is the proprietary *Cuphea* breeding selection coded W4591W, not patented, characterized by its bright pink-colored tubular flowers that fade to yellow-green color and have small dark purple-colored petals, light green-colored foliage, and moderately vigorous, spreading growth habit. The new cultivar was discovered and selected as a single flowering plant within the progeny of the above stated cross-pollination during November 2014 in a controlled environment in Guadalupe, Calif.

Asexual reproduction of the new cultivar by terminal stem cuttings since November 2014 in Guadalupe, Calif., Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balhoelrel' as a new and distinct cultivar of *Cuphea* plant:

1. Medium red and yellow-green colored tubular flowers having small dark purple-colored petals;
2. Dark green-colored foliage; and
3. Moderately vigorous, spreading growth habit.

Plants of the new cultivar differ from plants of the female parent primarily in having more flowers per plant, a different floral tube color, and a more spreading growth habit. Plants of the new cultivar differ from plants of the male parent primarily in having more flowers per plant and a darker floral tube color.

Of the many commercially available *Cuphea* cultivars, the most similar in comparison to the new cultivar is VERMILLIONAIRE 'Cupver', not patented. However, in side-by-side comparisons, plants of the new cultivar differ from plants of 'Cupver' in at least the following characteristics:

1. Plants of the new cultivar are shorter than plants of 'Cupver'; and
2. Plants of the new cultivar have flowers with more yellow-green coloration in the mature floral tubes than plants of 'Cupver'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balhoelrel'. The plants were approximately 3 months old and grown in 4.5-inch pots for approximately 8 weeks in a greenhouse in West Chicago, Ill. Plants were given one pinch at transplant.

DETAILED BOTANICAL DESCRIPTION

Figure 1:
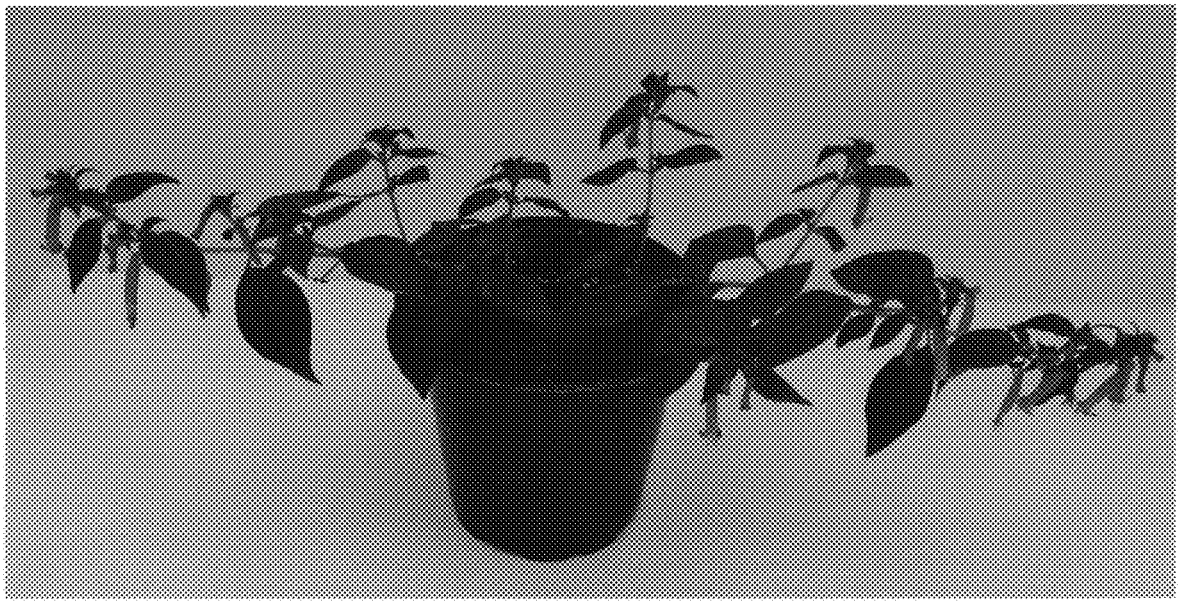
FIG. 1 illustrates a side view of the overall growth and flowering habit of 'Balhoelrel'.
Figure 2:
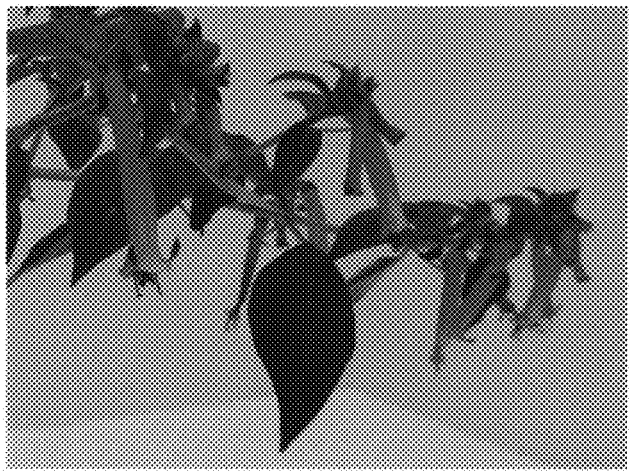
FIG. 2 illustrates a close-up view of flowers of 'Balhoelrel'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in March 2019 under natural light conditions in West Chicago, Ill.

The following descriptions and measurements describe approximately 3-month old plants produced from cuttings from stock plants and grown in a glass-covered greenhouse under conditions comparable to those used in commercial practice. The plants were grown in West Chicago, Ill. in 4.5-inch pots for approximately 8 weeks utilizing a soilless growth medium. Plants were given one pinch at transplant. Greenhouse temperatures were maintained at approximately 67° F. to 72° F. (19° C. to 22° C.) during the day and approximately 65° F. to 68° F. (18° C. to 20° C.) during the night. Supplemental lighting was used. Measurements and numerical values represent averages of typical plants.

Botanical classification: *Cuphea* hybrid 'Balhoelrel'.

Parentage:

*Female parent*.—Proprietary *Cuphea* breeding selection coded w14-0006, not patented.

*Male parent*.—Proprietary *Cuphea* hybrid breeding lection coded W4591W, not patented.

Propagation:

*Type cutting*.—Terminal stem.

*Time to initiate roots*.—Approximately 6 to 8 days.

*Time to produce a rooted cutting*.—Approximately 21 to 28 days.

*Root description*.—Fibrous, fine.

*Rooting habit*.—Freely branching.

Plant description:

*Commercial crop time*.—Approximately 6 to 8 weeks from a rooted cutting to finish in a 10 cm pot.

*Growth habit and general appearance*.—Annual, moderately vigorous, spreading.

*Hardiness*.—USDA Zone 9 (20° F. to 25° F./−6.7° C. to −3.9° C.).

*Size*.—Height from soil level to top of plant plane: Approximately 8.0 cm. Width: Approximately 38.0 cm.

*Branching habit*.—Freely branching, pinching enhances basal branching. Quantity of main branches per plant: Approximately 2.

*Branch*.—Strength: Strong, flexible. Length: Approximately 18.0 cm. Diameter: Approximately 2.0 mm. Length of central internode: Approximately 2.5 cm. Texture: Densely pubescent. Color of young stems: 146C. Color of mature stems: 146B tinted with 187A at nodes.

Foliage description:

*General description*.—Quantity of leaves per main branch: Approximately 14. Fragrance: None detected. Form: Simple. Arrangement: Opposite.

*Leaves*.—Aspect: Perpendicular to obtuse angle from stem. Shape: Ovate. Margin: Entire. Apex: Acute. Base: Rounded. Venation pattern: Pinnate. Length of mature leaf: Approximately 4.0 cm. Width of mature leaf: Approximately 2.5 cm. Texture of upper and lower surfaces: Moderately pubescent on venation only. Color of upper surface of young foliage: 137A with 139A near apex and venation of 147B. Color of lower surface of young foliage: Closest to but more grey than 147B with venation of 146D. Color of upper surface of mature foliage: 139A with venation of 147B. Color of lower surface of mature foliage: Closest to but more grey than 147B with venation of 146C.

*Petiole*.—Length: Approximately 1.2 cm. Diameter: Approximately 1.0 mm. Texture: Moderately pubescent. Color: 146C.

Flowering description:

*Flowering habit*.—'Balhoelrel' is freely flowering under outdoor growing conditions with substantially continuous blooming from spring through autumn and year-round in greenhouse environment.

*Lastingness of individual flower on the plant*.—Approximately 5 to 7 days.

Flower description:

*General description*.—Type: Single, calyx fused to a floral tube. Arrangement: Raceme of axillary and terminal flowers, downward facing. Quantity per plant: Approximately 40. Fragrance: None detected.

*Bud*.—Quantity per plant: Approximately 30.

*Bud just before opening*.—Shape: Oblong. Length: Approximately 5.0 mm. Diameter: Approximately 2.0 mm. Texture: Densely pubescent. Color: Upper half having tips of 137A, ridges of 146B, and grooves of NN155D; lower half having ridges of 146B with an overlay of 51B and grooves of 51D.

*Petals*.—Quantity: 2, at tip of floral tube, self-cleaning. Shape: Elliptic. Margin: Entire. Apex: Apiculate. Base: Attenuate. Length: Approximately 3.0 mm. Width: Approximately 1.0 mm. Texture of upper and lower surfaces: Glabrous. Color of upper surface when first and fully open: 83A with tip of NN155D. Color of lower surface when first and fully open: 83A with tip of NN155D.

*Floral tube*.—Shape: Six sepals fused into a tube with a basal hypanthium. Margin: Entire. Apex of sepals: Cuspidate. Length of floral tube to base of hypanthium: Approximately 2.2 cm. Length of free potion of sepal: Approximately 1.0 mm. Width of floral tube: Approximately 4.0 mm. Texture of inner surface: Glabrous. Texture of outer surface: Longitudinally grooved, densely pubescent primarily with very short hairs and sparse longer stiff hairs. Color of inner surface: NN155D. Color of outer surface: 51A tinted with 44A, 2B with N144A near tube opening and tips of 137A.

*Hypanthium*.—Aspect: Horizontal. Shape: Saccate. Length: Approximately 4.0 mm. Width: Approximately 4.0 mm. Texture of outer surface: Densely pubescent with very short hairs. Texture of inner surface: Glabrous. Color of inner surface: NN155D. Color of outer surface: 51A.

*Peduncle*.—Strength: Strong, flexible. Aspect: Acute angle to stem. Length: Approximately 1.0 cm. Diameter: Approximately 1.0 mm. Texture: Densely pubescent. Color: 146D.

*Reproductive organs*.—Androecium: Stamen quantity: 11, dorsifixed, adnate to floral tube. Stamen length of free portion: Approximately 5.0 mm, 2 at 3.0 mm. Filament color: 187A. Anther shape: Oblong. Anther length: Approximately 1.0 mm. Anther color: N92A. Pollen amount: Moderate. Pollen color: NN155A. Gynoecium: Pistil quantity: 1 per flower. Pistil length: Approximately 2.1 cm. Stigma shape: Capitate. Stigma length: Less than 1.0 mm. Stigma color: NN155A. Style length: Approximately 1.4 mm. Style color: N79C fading toward ovary. Ovary length: Approximately 7.0 mm. Ovary color: NN155D.

Seed and fruit production: Neither seed nor fruit production has been observed.

Disease and pest resistance: Resistance to pathogens and pests common to *Cuphea* has not been observed.

What is claimed is:

1. A new and distinct cultivar of *Cuphea* plant named 'Balhoelrel', substantially as herein illustrated and described.

* * * * *